United States Patent
Gurny et al.

(10) Patent No.: US 6,589,999 B2
(45) Date of Patent: Jul. 8, 2003

(54) ANTIBACTERIAL AQUEOUS OPHTHALMIC FORMULATIONS CONTAINING OFLOXACIN AND USE OF CHITOSAN FOR SOLUBILIZING OFLOXACIN SUSPENDED IN AN AQUEOUS MEDIA

(75) Inventors: Robert Gurny, Geneva (CH); Olivia Mireille Felt, St.-Julien-en-Genevois (FR)

(73) Assignee: Laboratoire Medidom S.A., Geneva (CH)

( * ) Notice: Subject to any disclaimer, the term of this patent is extended or adjusted under 35 U.S.C. 154(b) by 0 days.

(21) Appl. No.: 09/859,908

(22) Filed: May 17, 2001

(65) Prior Publication Data

US 2002/0002148 A1 Jan. 3, 2002

(30) Foreign Application Priority Data

May 26, 2000 (EP) .............................. 00111377

(51) Int. Cl.[7] ............................... A61K 47/00
(52) U.S. Cl. ..................... 514/777; 514/252.1; 514/912
(58) Field of Search .............................. 514/777, 252.1, 514/912

(56) References Cited

U.S. PATENT DOCUMENTS 5,422,116 A * 6/1995 Yen et al. ................... 424/427

* cited by examiner

Primary Examiner—Zohreh Fay
(74) Attorney, Agent, or Firm—Clifford W. Browning; Woodard, Emhardt, Moriarty, McNett & Henry LLP

(57) ABSTRACT

The aqueous ophthalmic formulation for the treatment and prevention of infections contains ofloxacin as active ingredient and a chitosan having a weight average molecular weight of 500,000–5,000,000 Daltons and a deacetylation degree of 30–90% as solubilizing agent of ofloxacin. Chitosan having a deacetylation degree of 30–90% may be also used for solubilizing ofloxacin suspended in an aqueous media having a substantially neutral pH in any other applications.

17 Claims, No Drawings

ANTIBACTERIAL AQUEOUS OPHTHALMIC FORMULATIONS CONTAINING OFLOXACIN AND USE OF CHITOSAN FOR SOLUBILIZING OFLOXACIN SUSPENDED IN AN AQUEOUS MEDIA

This Application claims the benefit of European Patent Application No. 00 111 377.8 filed May 26, 2000.

BACKGROUND OF THE INVENTION

The invention relates to an antibacterial aqueous ophthalmic formulation containing ofloxacin as an active ingredient and to the use of chitosan for solubilizing ofloxacin suspended in an aqueous media.

Ofloxacin [i.e. racemic (±)-9-fluoro-3-methyl-10-(4-methyl-1-piperazinyl)-7-oxo-2,3-dihydro-7H-pyrido[1,2,3-de][1,4]benzoxazine-6-carboxylic acid], first disclosed by Daiichi Seiaku CO., LTD in EP-A-0,047,005, is known to be an excellent antibacterial agent which is active against a broad spectrum of gram positive and gram negative organisms.

The high antibacterial action of ofloxacin has been explained by its potent inhibitory activities against DNA gyrase in bacterial cells (Sato K, Inoue Y, Fujii T, Aoyama H, Mitsuhashi S, *Infection* 1986, 14 Suppl 4:S226–30).

Ofloxacin has been disclosed to be useful for treating a wide variety of bacterial ocular infections by topical administration.

However, due to the poor solubility of ofloxacin which is as low as 3.23 mg/ml at pH of 7.0 [Ross et al, Int. J. Pharm, 63:237–250 (1990)], the use of ofloxacin in ophthalmic formulations meets some problems.

In ophthalmic formulations, solubility of ofloxacin is known to be increased by including additives, in particular surfactants.

However, surfactants are known to cause corneal damage when used for prolonged period.

The solubility of ofloxacin has been disclosed by Ross et al, Int. J. Pharm, 63:237–250 (1990) as being 95,4 mg/ml at pH of 5.0, and the solubility of ofloxacin is further known to be increased by decreasing the pH of the aqueous formulation at a pH close to 5.0, in particular with hydrochloric acid.

EP-A-0,275,515 discloses an aqueous pharmaceutical composition for the treatment of infections in the form of eye-drops comprising an effective amount of S-ofloxacin (levofloxacin) said to be the active and more soluble form of ofloxacin, and an aqueous vehicle such as water in which may be incorporated additives such as surfactants, stabilizers, solubilizers, pH adjusting agents, and so on. The preparation example of eye-drops mentions in particular the use of benzalkonium chloride as a stabilizer and sodium chloride, sodium hydroxide and hydrochloric acid as additives.

An existing collyrium marketed for example in Switzerland under the name Floxal® and provided from Chauvin, Montpellier, France is presented in the form of a solution containing 0.3% ofloxacin, benzalkonium chloride, and unspecified collyrium additives.

EP-A-0,274,714 discloses an eye ointment for the treatment of infectious eye diseases in the form of a hydrogel containing ofloxacin as active ingredient and carboxymethylcellulose as gelifying agent. Preparation of the ointment requires a step of adjusting the pH of a solution containing ofloxacin at a value of 5.0 to 5.5 with aqueous hydrochloric acid solution and aqueous sodium hydroxide solution.

BRIEF SUMMARY OF THE INVENTION

An object of the present invention is to provide an aqueous ophthalmic formulation containing ofloxacin for curing infections, without problems of tolerance even for prolonged use, which does not contain surfactants and which avoids the steps of adjusting and verifying pH during preparation of the formulation.

Another object of the present invention is to provide the use of a chitosan having a deacetylation degree of 30–90% for solubilizing ofloxacin suspended in an aqueous media having a substantially neutral pH.

According to the present invention, these object have been achieved as a result of the surprising finding that the addition of a chitosan in an aqueous solution containing ofloxacin solubilizes ofloxacin in an optimal way.

Chitosan is known as a chitin derivative obtained by partial to substantial deacetylation of chitin also named poly(N-acetyl-D-glucosamine), which is a naturally occurring biopolymer found in shellfish.

Chitosan contains free amine ($—NH_2$) groups and may be characterised as to the proportion of N-acetyl-D-glucosamine units and D-glucosamine units, and such is expressed as the degree of deacetylation of the fully acetylated polymer chitin.

U.S. Pat. No. 5,422,116 discloses that chitosan having a deacetylation degree of 60 to 99% is useful for preparing a liquid ophthalmic aqueous sustained release delivery system which provides a slow and sustained release of the treating agents incorporated therein to the eye.

In the present invention, an aqueous ophthalmic formulation for the treatment and prevention of infections contains ofloxacin as active ingredient and a chitosan having a deacetylation degree of 30–90% and a molecular weight of 500,000–5,000,000 Da as solubilizing agent of ofloxacin.

The present invention provides an aqueous ophthalmic formulation containing ofloxacin and chitosan without further addition of surfactants or other solubilizing agents or other additives such as pH adjusting agents, which can cure ocular infections, which can be used without problems of tolerance even for a prolonged treatment, and which simultaneously presents increased lachrymal availability and increased time of efficacy with respect to a commercial solution containing ofloxacin.

Other advantages of the present invention will appear in the following detailed description.

Ofloxacin which can be used in the present invention may be commercially available (for example from Sigma, Buchs, Switzerland) or can be prepared according to various known synthetic processes including the process disclosed by Daiichi Seiaku CO., LTD in EP-A-0,047,005.

The ofloxacin may be either in the racemate form or in the form of its active S-isomer [S-(−)-9-fluoro-3-methyl-10-(4-methyl-1-piperazinyl)-7-oxo-2,3-dihydro-7H-pyrido[1,2,3-de][1,4]benzoxazine-6-carboxylic acid].

The aqueous ophthalmic formulation of the present invention preferably comprises from 0.1 to 0.5 wt/v % ofloxacin, based on the total aqueous ophthalmic formulation.

An aqueous ophthalmic formulation having a content of ofloxacin lower than 0.1 wt/v % is not advantageous because the antibacterial effect becomes insignificant.

An aqueous ophthalmic formulation having a content of ofloxacin higher than 0.5 wt/v % is not advantageous because the presence of ofloxacin at these concentrations may cause undesired side-effects such as irritation and intolerance.

Preferably, the ofloxacin is contained in an amount of 0.3–0.5 wt/v %, and more preferably in an amount of 0.3%, based on the total aqueous ophthalmic formulation.

Chitosans contained in the aqueous ophthalmic formulation of the present invention have a weight average molecular weight of 500,000–5,000,000 Daltons and a deacetylation degree of 30–90%.

It is to be noted that in the present description and claims, the term chitosan means indifferently a chitosan salt or chitosan base.

Chitosan salt means a chitosan containing ammonium —($NH_3^+$) groups with corresponding counterions ($X^-$) instead of free amine (—$NH_2$) groups.

A deacetylation degree of 30–90% means that the chitosan comprises 30–90% of D-glucosamine units or D-glucosammonium salt units and 70–10% of N-acetyl-D-glycosamine units, respectively.

Chitosan which can be used in the present invention is commercially available or can be prepared by a process based on deacetylation of chitin until the desired deacetylation degree, e.g. as described by Roberts, G. A. F., in "Chitin chemistry", Mc Millan Press LTD, Houndmills, p. 64–82 (1992), to obtain a chitosan including free amine groups.

Commercial sources of chitosan are for example Pronova® Biopolymer, Drammen, Norway; Vanson Company, Redmond, Wash., USA; Nova Chem Limited, Armdale, Halifax, Nova Scotia, Canada; Biosynth A. G., Staad, Switzerland; Biopolymer Engineering, Inc., St-Paul, Minn., USA.

The weight average molecular weight of chitosan used in the present invention may be determined by size exclusion chromatography as mentioned hereafter.

Chitosans having a weight average molecular weight lower than 500,000 Daltons are not appropriate for use in aqueous ophthalmic formulations because they would lead to formulations with insufficient bioavailability and poor residence time of the ofloxacin in the eye.

Chitosans of weight average molecular weights greater than 5,000,000 Daltons are not appropriate for use in aqueous ophthalmic formulations since they imply high manufacturing costs and also since they form very stiff gels which cannot be easily and reproducibly applied topically.

Preferably, chitosans contained in the aqueous ophthalmic formulation of the present invention have a molecular weight of 1,000,000–2,000,000 Daltons.

However, when used in other applications for solubilizing ofloxacin suspended in an aqueous media having a substantially neutral pH, chitosan having any weight average molecular weight may be used since in term of solubilization capacity, low molecular weight chitosans exert identical effect than high molecular weight chitosans.

The deacetylation degree of chitosan may be determined by a spectrophotometric method such as described in the literature by Muzarelli, R. A. and Ricchetti, R., in Carbohydr. Polym. 5, p. 461–472, 1985 or Muzarelli, R. A. and Richetti, R. in "Chitin in Nature and Technology", Plenum Press, p. 385–388, 1986.

Chitosans having a deacetylation degree lower than 30% are not appropriate in the present invention because the number of amine groups able to be ionized at physiological pH is insufficient. As such, the ionic interaction between chitosan and the mucus on one hand and between chitosan and ofloxacin on the other hand is considerably reduced, thereby decreasing the mean residence time of the formulation as well as its pharmacokinetic performances.

Chitosans having a deacetylation degree higher than 90% are not appropriate in the present invention because the solubility of the polysaccharide is diminished when increasing the deacetylation degree.

Preferably, chitosan used in the present invention has a deacetylation degree lower than 60%.

Preferably, the aqueous ophthalmic formulation of the present invention comprises from 0.1 to 3 wt/v % of chitosan.

An aqueous ophthalmic formulation having a content of chitosan lower that 0.1 wt/v % is not advantageous because at these concentrations, it does not significantly prolong the residence time.

An aqueous ophthalmic formulation having a content of chitosan higher than 3 wt/v % is not advantageous because the presence of chitosan at these concentrations may cause discomfort. Also, the viscosity of the formulation may be too high to allow easy and repeatable administration.

Preferably, the chitosan is used in an amount of 0.1–1.5 wt/v %, and more preferably in an amount of 0.5 wt/v %, based on the total aqueous ophthalmic formulation.

Preferably, the aqueous ophthalmic formulation according to the present invention should have a viscosity not higher than 600 mPa.s.

A formulation having a viscosity higher than 600 mPa.s is not advantageous, because it forms a stiff gel which is not readily applied topically.

For the purpose of the invention, the concentration of chitosan in the aqueous ophthalmic formulation of the present invention is adjusted to optimize the bioavailability and precorneal residence time of ofloxacin.

The aqueous ophthalmic formulation of the present invention may be prepared according to conventional techniques for example as follows.

Chitosan salt is dissolved in a phosphate buffer (PBS) pH 7.4. Separately, ofloxacin is suspended in a phosphate buffer (PBS) pH 7.4. After complete dissolution of chitosan, the chitosan solution is poured into the suspension containing ofloxacin in order to obtain the final formulation wherein ofloxacin is solubilized.

If chitosan base is used, it should be previously swelled in a small amount of acetic acid 1% before to be dissolved in PBS pH 7.4.

Ofloxacin, which was insoluble in PBS pH 7.4 becomes soluble due to the presence of chitosan.

The aqueous ophthalmic formulation thus obtained has a pH of 5.5 to 6.5 and an osmolality of 240–340 mosm/kg, thus providing physiological acceptance.

Thus, solubilization of ofloxacin is performed in a single step, which represents a great advantage in the production of the aqueous ophthalmic formulation of the present invention.

The aqueous ophthalmic formulation of the present invention may be packaged either in monodose units or in multidose containers.

The aqueous ophthalmic may be administered by instillation in the eye in convenient drop form.

Formulations according to the present invention are particularly useful to treat or prevent bacterial infections of the anterior segment of the eye and related structure such as conjunctivitis, blepharitis, blepharoconjunctivitis, keratitis and keratoconjunctivitis.

The examples below will illustrate the present invention without limiting its scope in any way.

Detailed Description of the Invention

To illustrate the advantages of the aqueous ophthalmic formulations of the present invention, various formulations containing 0.3% ofloxacin and various chitosans have been tested for availability of ofloxacin in the lachrymal fluid and for time of efficacy.

Materials Used to Prepare Formulations to be Tested

Commercial ophthalmic formulation containing 0.3% ofloxacin used in the tests as a comparative formulation is Floxal® commercially available from Chauvin (Montpellier, France).

Ofloxacin used to prepare aqueous ophthalmic formulations according to the present invention and a comparative formulation is Ofloxacin from Sigma (Buchs, Switzerland).

Chitosan used to prepare the comparative formulation is:

UPCl 110: high purity grade chitosan hydrochloride (provided by Pronova Biopolymer (Oslo, Norway)) having a deacetylation degree of 87% and a molecular weight of 160,000 Daltons.

Chitosans used to prepare formulations according to the present invention are:

UPG 210: high purity grade chitosan glutamate (provided by Pronova Biopolymer (Oslo, Norway) having a deacetylation degree of 83% and a molecular weight of 580,000 Daltons.

CHITO-1: chitosan base (provided by Ciba Vision® (Duluth, Ga., USA) having a deacetylation degree of 53% and a molecular weight of 1,350,000 Daltons.

CHITO-2: chitosan base (provided by Ciba Vision® (Duluth, Ga., USA) having a deacetylation degree of 59% and a molecular weight of 1,930,000 Daltons.

The deacetylation degree of each above chitosan has been provided by the supplier and has been verified by UV spectrophotometry according to the method described in the literature by Muzarelli, R. A. and Ricchetti, R., in Carbohydr. Polym. 5, p. 461–472, 1985 or Muzarelli, R. A. and Richetti, R. in "Chitin in Nature and Technology", Plenum Press, p. 385–388, 1986.

The molecular weight of each chitosan as reported above has been determined by size exclusion chromatography, with a Waters 600 E apparatus, combined with an autosampler (Waters TM717plus) and a Waters 410 differential refractometer. The conditions of analysis were the following:

Column: series of 4 columns Ultrahydrogel® (7.8×300)
Temperature: 30° C.
Flow rate: 0.8 ml/min
Eluent: acetate buffer pH 4.2
Standard: pullulan 0.1% solution of chitosan in acetate buffer pH 7.4 was injected five times.

Rheological measurements have been made with a Bohlin Rheometer CS equipped with a system of control of the temperature (CS ETO). Data have been obtained under the following conditions:

Temperature: 25° C.
Measuring system: Cone-plate 4/40 LS
Shear stress: 5.97E-2 Pa
Oscillation test Rheological evaluation as reported in the following Table 1 has been tested at a concentration of 1.5% in a phosphate buffer pH 7.4 for UPCl 110 and UPG 210, and at a concentration of 0.5% in acetic acid 1% for CHITO-1 and CHITO-2.

Phosphate buffer solution (PBS) pH 7.4 used to prepare formulations according to the present invention and comparative formulation is prepared as follows. Sodium chloride (8.5 g), sodium hydrogenophosphate (280 mg), sodium dihydrogenophosphate (40 mg) were dissolved in distilled water (1 liter). The solution is then sterilized by autoclaving at 121° C. during 15 minutes according to the requirements of the European Pharmacopoeia.

Preparation of Formulations to be Tested

Chitosan, in an appropriate amount for a concentration of 1.5% w/v or 0.5% in the final formulation, is dissolved at room temperature under magnetic stirring in isocryoscopic sterile phosphate buffer solution (PBS) pH 7.4.

Separately, ofloxacin, in an amount appropriate for a concentration of 0.3% in the final formulation, is suspended in isocryoscopic sterile phosphate buffer solution (PBS) pH 7.4.

After complete dissolution of chitosan (about 1–2 days for chitosan having a molecular weight higher that 1,000,000 Daltons), the solution of chitosan is poured into the suspension containing ofloxacin under magnetic stirring. If required, PBS pH 7.4 was added to complete volume.

After a few minutes, ofloxacin, which was not soluble in PBS pH 7.4, becomes soluble due to the presence of chitosan, and the formulation to be tested is kobtained.

It is assumed that this solubilization phenomena is due to the fact that aqueous solution of chitosan have a pH ranging from 5.5 to 6.5.

Thus, solubility of ofloxacin would be increased by decreasing the pH of the solution from 7.4 to 5.5–6.5.

Formulations prepared as above and submitted to the tests below are shown in the following Table 1, wherein Control is Floxal®, Comp. 1 is a comparative formulation and Formulations 1, 2, and 3 are formulations according to the present invention.

TABLE 1

| Formulation | Ofloxacin quantity (%) | Chitosan type | MW (Daltons) | deacetylation degree (%) | quantity (%) | viscosity (mPa.s) |
|---|---|---|---|---|---|---|
| Control | 0.3 | — | — | — | — | 3.0 |
| Comp. 1 | 0.3 | UPCl 110 | 160,000 | 87 | 1.5 | 30.7 |
| 1 | 0.3 | UPG 210 | 580,000 | 83 | 1.5 | 114.2 |
| 2 | 0.3 | CHITO-1 | 1,350,000 | 53 | 0.5 | 73.7 |
| 3 | 0.3 | CHITO-2 | 1,930,000 | 59 | 0.5 | 477.1 |

It is to be noted that formulations with CHITO-1 and CHITO-2 at concentrations higher than 0.5% w/v were not tested since they lead to the formation of hydrogels of viscosity too high to be easily and reproducibly applied to the eye.

Pharmacokinetic Evaluation of Formulations Containing Ofloxacin

Experimental Protocol

Male albino New Zealand rabbits weighing approximately 4–5 kg and free of any ocular damage were used throughout the whole study as approved by the local Ethics Committee for animal experimentation.

A volume of 25 µl of the formulation to be tested was administered by instillation onto the cornea of an unaesthetized animal using an adjustable micropipette, Assipettor-Digital® (Assistent, Germany).

Tear samples were collected after 0, 1, 2, 4, 6, 8, 10, 15 20, 30, 45 and 60 minutes after instillation, using 2.0 µl calibrated glass capillaries (microcaps Drummond®, Thomas Scientific™, Swedesboro, N.J., USA). Samples were frozen at −25° C. for further analysis of drug concentrations in tears.

Each formulation was tested on six rabbits.

Determination of Ofloxacin Concentration in Tears Using Capillary Electrophoresis Determination of ofloxacin in tears was carried out on a HP$^{3D}$CE system (Hewlett-Packard, Wilmington, Del., USA), as described earlier [V. Baeyens, E. Varesio, J-L. Veuthey et al, "Determination of dexamethassone in tears by capillary electrophoresis"; J. Chrom. B. 1997; 692; 222–226].

The system consists of a capillary electrophoresis unit equipped with a diode array detector (DAD), an autosampler and a high-velocity air-cooled capillary cartridge.

HP3D Chemstation software was used for instrument control, data acquisition and data analysis.

Hewlett-Packard capillaries with a 50 μm internal diameter (I.D.) (375 μm O.D.), 64.5 cm total length (56 cm from inlet to the detector window) were used for all experiments. These capillaries were made of fused-silica and equipped with an extended path-length detection window of 150 μm I.D. ("bubble cell"). New capillaries were flushed for 3 minutes with 1M NaOH, followed by 5 min. with 0.1M NaOH, and finally 10 min. with water. After each run, capillaries were flushed with water, 2 min. with 0.1M sodium dodecyl sulphate, then 2 min. with water and finally 4 min. with the separation buffer solution. The 100 mM phosphate buffer solution used for the separation was prepared as described in the Ph.Helv.VII by dissolving 6.75 g of $KH_2PO_4$ in 500 ml of water to obtain a pH of 4.5.

Preparation of tear samples was carried out as follows.

A micro-vial (Hewlett-Packard, Waldbronn, Germany) was filled with 18 μl of water containing only 10% (v/v) of separation buffer to enhance sensitivity by stacking method and 10 μg.ml$^{-1}$ of imipramine HCl used as internal standard. Then a tear sample of 2 μl collected with the glass capillary was blown under a gently nitrogen flow into the micro-vial. The vial was finally centrifuged for 5 min. at 10,000 rpm (Avanti™ 30 Centrifuge, Beckman) before injection.

Samples (24 nl) were injected under pressure (5 kPa for 20 s) and electrophoresis was performed at a constant voltage of 20 kV (310 V cm–1) after 1 min. ramp step to avoid loss of sample at the injection [K. D. Altria; "Main component assay of pharmaceutical by capillary electrophoresis: Considerations regarding precision, accuracy, and linearity data"; J. Capill. Electrophor. 1996; 3; 13]. The capillary was thermostated at 25° C. and the detection was performed using the DAD (scanning from 190 nm to 600 nm).

Electrophoregrams were monitored at 290 nm with a bandwidth of 3 nm for both ofloxacin and imipramine. In order to subtract the detector noise, the reference signal was fixed at 450 nm (bandwidth=80 nm). In all experiments, areas were corrected by their respective migration times.

Data Analysis

The three following parameters have been calculated from the different time-concentration curves obtained after measuring the amount of ofloxacin in tears:

Area under the curve values ($AUC_{eff}$), which represents the availability of ofloxacin in the lacrymal fluid, calculated using trapezoidal rule.

$AUC_{eff}$ chitosan formulation/$AUC_{eff}$ control which represents the performance of the formulation.

Time of efficacy ($t_{eff}$), the time during which the concentration of ofloxacin remains above its $MIC^{90}$ (minimal inhibitory concentration) value, i.e. above 4 μg/ml.

Comparison of these pharmacokinetic parameters between the different formulations tested and the control was achieved using a Students t-test (unpaired samples), after ensuring that the data points followed a normal distribution.

The results are shown in the following Table 2.

TABLE 2

| Formulation | $AUC_{eff} \pm SD$ (μg/ml min) | AUC ratio | $t_{eff} \pm SD$ (min) |
|---|---|---|---|
| Control (Floxal ®) | 3534 ± 2373 | — | 25 ± 15 |
| Comp. 1 | 1746 ± 605 | 0.49 | 14 ± 6.5 |
| 1 | 5306 ± 2139 | 1.5 | 27 ± 11 |
| 2 | 5812 ± 2794 | 1.64[a] | 37 ± 8[a] |
| 3 | 11543 ± 4547 | 3.27[a] | 46 ± 22[a] |

[a]p < 0.05, Student's test, unpaired samples, comparison with control

These results demonstrate that chitosan having a weight average molecular weight higher than 500,000 significantly improves ofloxacin availability in tears, the $AUC_{eff}$ ratio showing about 1,5 to 3,2-fold improvement.

The most marked effect is observed with Formulation 3 containing CHITO-2 having a weight average molecular weight of 1,930,000 Daltons and a deacetylation degree of 59%.

These results also demonstrate that chitosan having a weight average molecular weight higher than 500,000 improves time of efficacy of ofloxacin, the most marked effect being also observed with Formulation 3 which shows about 1,8-fold improvement. An advantage for the patient is that only 2 daily instillations are required instead of 4 for Floxal®.

Example of an Aqueous Ophthalmic Formulation According to the Present Invention.

0.025 g of chitosan CHITO-1 as referred above, having a molecular weight of 1,350,000 and a deacetylation degree of 53% was swelled in 0.25 ml of acetic acid 1% and then dissolved at room temperature under magnetic stirring in about 2 ml of an isocryoscopic sterile phosphate buffer solution (PBS) pH 7.4 as referred above.

Separately, 0,015 g of ofloxacin as referred above was suspended in about 1 ml of an isocryoscopic sterile phosphate buffer solution (PBS) pH 7.4 as referred above.

After complete dissolution of chitosan, the solution containing chitosan was poured into the suspension containing ofloxacin under magnetic stirring and the volume is completed to 5 ml with isocryoscopic sterile phosphate buffer solution (PBS) pH 7.4 as referred above.

After a few minutes, ofloxacin became soluble.

Five ml of a formulation according to the present invention containing 0.5% w/v and 0.3% w/v of ofloxacin were thus obtained.

The formulation was odourless, clear and slightly yellow in colour.

The osmolality of the formulation was 290 mosm/kg.

The pH of the formulation was 6.25.

The formulation thus obtained may be packaged either in monodose units or in multidose container.

The formulation may be topically administered by instillation in the eye in convenient drop form.

Thus, the presence of chitosan in an aqueous ophthalmic formulation containing ofloxacin simultaneously allows solubilisation of ofloxacin and the increase of the pharmacokinetic parameters of ofloxacin.

No addition of a surfactant is required and the formulation is very easy to prepare since the pH does not need to be adjusted with pH-adjusting agents.

The presence of chitosan allows the incorporation of ofloxacin in higher quantities than those found in commercial formulations, while maintaining pH values compatible with ocular administration, and with the advantages of having increased pharmacokinetic parameters and increased clinical efficacy due to the higher ofloxacin concentration.

According to the present invention, chitosan may be used not only as solubilizing agent of ofloxacin for the preparation of an aqueous ophthalmic formulation containing ofloxacin for treating bacterial infections, but also for solubilizing ofloxacin suspended in any aqueous media having a substantially neutral pH in any other applications requiring the solubilization of ofloxacin.

In this latter case, only the deacetylation degree of chitosan is critical since in term of solubilization capacity, low molecular weight chitosans exert identical effect than high molecular weight.

What is claimed is:

1. An aqueous ophthalmic formulation for the treatment and prevention of infections containing ofloxacin as active ingredient and a chitosan having a weight average molecular weight of 500,000–5,000,000 Daltons and a deacetylation degree of 30–90% as solubilizing agent of ofloxacin.

2. The aqueous ophthalmic formulation according to claim 1, characterized in that it contains from 0.1 to 0.5 wt/v ofloxacin, based on the total aqueous formulation.

3. The aqueous ophthalmic formulation according to claim 2, characterized in that it contains from 0.3 to 0.5 wt/v ofloxacin, based on the total aqueous formulation.

4. The aqueous ophthalmic formulation according to claim 3, characterized in that it contains 0.3 wt/v ofloxacin, based on the total aqueous formulation.

5. The aqueous ophthalmic formulation according to claim 1, characterized in that the chitosan has a molecular weight of 1,000,000–2,000,000 Daltons.

6. The aqueous ophthalmic formulation according to claim 1, characterized in that the chitosan has a deacetylation degree lower than 60%.

7. The aqueous ophthalmic formulation according to claim 1, characterized in that it contains from 0.1 to 3.0 wt/v of chitosan, based on the total aqueous ophthalmic formulation.

8. The aqueous ophthalmic formulation according to claim 7, characterized in that it contains from 0.1 to 1.5 wt/v of chitosan, based on the total aqueous ophthalmic formulation.

9. The aqueous ophthalmic formulation according to claim 8, characterized in that it contains 0.5 wt/v of chitosan, based on the total aqueous ophthalmic formulation.

10. The aqueous ophthalmic formulation according to claim 1, characterized in that it has a viscosity not higher than 600 mPa.s.

11. The aqueous ophthalmic formulation according to claim 1, being packaged in monodose units.

12. The aqueous ophthalmic formulation according to claim 1, being packaged in multidose container.

13. A process for the preparation of an aqueous ophthalmic formulation for treating bacterial infections containing ofloxacin as the active ingredient, comprising the step of solubilizing ofloxacin suspended in an aqueous media having a substantially neutral pH by adding to the ofloxacin suspended in the aqueous media having a substantially neutral pH a chitosan having a weight average molecular weight of 500,000–5,000,000 Daltons and a deacetylation degree of 30–90% as the solubilizing agent.

14. A process for the preparation of an aqueous ophthalmic formulation for treating conjunctivitis, blepharitis, blepharoconjunctivitis, keratitis and keratoconjunctivitis containing ofloxacin as the active ingredient, comprising the step of solubilizing ofloxacin suspended in an aqueous media having a substantially neutral pH by adding to the ofloxacin suspended in the aqueous media having a substantially neutral pH a chitosan having a weight average molecular weight of 500,000–5,000,000 Daltons and a deacetylation degree of 30–90% as the solubilizing agent.

15. A process for solubilizing ofloxacin suspended in an aqueous media having a substantially neutral pH, comprising the step of adding to the ofloxacin suspended in the aqueous media having a substantially neutral pH a chitosan having a deacetylation degree of 30–90% as the solubilizing agent.

16. An aqueous ophthalmic formulation, comprising chitosan having a deacetylation degree of 30–90% as a solubilizing agent for ofloxacin suspended in an aqueous media having a substantially neutral pH.

17. An aqueous ophthalmic formulation of claim 1 for treating conjunctivitis, blepharitis, blepharoconjunctivitis, keratitis and keratoconjunctivitis.

* * * * *